United States Patent
Werneth et al.

(10) Patent No.: US 9,439,721 B2
(45) Date of Patent: *Sep. 13, 2016

(54) BI-MODAL LINEAR AND LOOP ABLATION CATHETER, AND METHOD

(75) Inventors: Randell Werneth, San Diego, CA (US); Ricardo Roman, San Diego, CA (US); Timothy J. Corvi, Carlsbad, CA (US); Betty Hu, La Jolla, CA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 454 days.

This patent is subject to a terminal disclaimer.

(21) Appl. No.: 12/546,750

(22) Filed: Aug. 25, 2009

(65) Prior Publication Data

US 2011/0054464 A1    Mar. 3, 2011

(51) Int. Cl.
*A61B 18/14* (2006.01)
*A61B 17/00* (2006.01)
*A61B 18/00* (2006.01)

(52) U.S. Cl.
CPC ...... *A61B 18/1492* (2013.01); *A61B 2017/003* (2013.01); *A61B 2018/00797* (2013.01); *A61B 2018/00821* (2013.01); *A61B 2018/1407* (2013.01)

(58) Field of Classification Search
USPC .................................................. 604/525, 528
See application file for complete search history.

(56) References Cited

U.S. PATENT DOCUMENTS

| | | | |
|---|---|---|---|
| 5,308,342 A * | 5/1994 | Sepetka et al. | 604/525 |
| 5,322,064 A * | 6/1994 | Lundquist | A61B 18/1492 600/381 |
| 5,358,479 A * | 10/1994 | Wilson | 604/95.04 |
| 5,555,883 A | 9/1996 | Avitall | |
| 5,619,993 A * | 4/1997 | Lee | A61M 25/0041 600/146 |
| 5,730,127 A | 3/1998 | Avitall | |
| 5,820,591 A * | 10/1998 | Thompson et al. | 604/95.01 |
| 5,855,560 A * | 1/1999 | Idaomi | A61B 18/1492 600/433 |
| 6,077,258 A * | 6/2000 | Lange et al. | 604/527 |
| 6,156,053 A * | 12/2000 | Gandhi | A61M 25/1011 604/101.02 |

(Continued)

FOREIGN PATENT DOCUMENTS

| | | |
|---|---|---|
| WO | 2006091597 A1 | 8/2006 |
| WO | 2010028053 A1 | 3/2010 |

(Continued)

OTHER PUBLICATIONS

Calkins, Hugh et al. "A New System for Catheter Ablation of Atrial Fibrillation." The American Journal of Cardiology, vol. 83 (1999) 227D-236D.

(Continued)

*Primary Examiner* — Jaymi Della
(74) *Attorney, Agent, or Firm* — Christopher & Weisberg, P.A.

(57) ABSTRACT

Medical devices, systems, and methods for treating patients with tissue ablation include catheter systems having bi-modal steering mechanisms, which are capable of both linear and loop ablation. In other words, the catheter system may have two different steering modes: two-dimensional and three-dimensional. In the first and second steering modes, the steering actuator may cause one or more portions of the catheter shaft to bend in different planes. A steerable ablation catheter may include treatment elements such as electrodes at its distal end and along the catheter shaft, each of which may map, pace, and ablate. Optional features include a series of thermocouples for monitoring local temperatures.

12 Claims, 14 Drawing Sheets

(56) References Cited

U.S. PATENT DOCUMENTS

| | | |
|---|---|---|
| 6,287,301 B1 | 9/2001 | Thompson et al. |
| 6,413,234 B1 | 7/2002 | Thompson et al. |
| 6,585,717 B1 * | 7/2003 | Wittenberger et al. ....... 604/523 |
| 2001/0039413 A1 | 11/2001 | Bowe |
| 2002/0068868 A1 | 6/2002 | Thompson et al. |
| 2002/0156452 A1 * | 10/2002 | Pursley ............. A61M 25/0017 604/500 |
| 2003/0144657 A1 | 7/2003 | Bowe et al. |
| 2004/0147827 A1 * | 7/2004 | Bowe ............................ 600/374 |
| 2004/0231683 A1 | 11/2004 | Eng et al. |
| 2004/0243102 A1 * | 12/2004 | Berg et al. .................... 604/525 |
| 2006/0241366 A1 * | 10/2006 | Falwell et al. ................ 600/374 |
| 2006/0265004 A1 * | 11/2006 | Callaghan .......... A61B 17/0057 606/213 |
| 2007/0100235 A1 * | 5/2007 | Kennedy ................ A61B 6/504 600/434 |
| 2008/0281312 A1 | 11/2008 | Werneth et al. |
| 2009/0149848 A1 | 6/2009 | Werneth et al. |
| 2010/0057072 A1 | 3/2010 | Roman et al. |
| 2010/0057073 A1 | 3/2010 | Roman et al. |
| 2010/0057074 A1 | 3/2010 | Roman et al. |

FOREIGN PATENT DOCUMENTS

| | | |
|---|---|---|
| WO | 2010028059 A1 | 3/2010 |
| WO | 2010028063 A2 | 3/2010 |

OTHER PUBLICATIONS

Gauri, Andre J. et al. "Catheter Ablation for Atrial Fibrillation." Indian Pacing and Electrophysiology Journal. (2003) 210-223.

Matsuo, Seiichiro et al. "Ablation of Chronic Atrial Fibrillation." Heart Rhythm Journal. Nov. 2007 1461-1463.

Nadamanee, Koonlawee et al. "A New Approach for Catheter Ablation of Atrial Fibrillation: Mapping of the Electrophysiologic Substrate." Journal of the American College of Cardiology, vol. 43 (2004) 2044-2053.

* cited by examiner

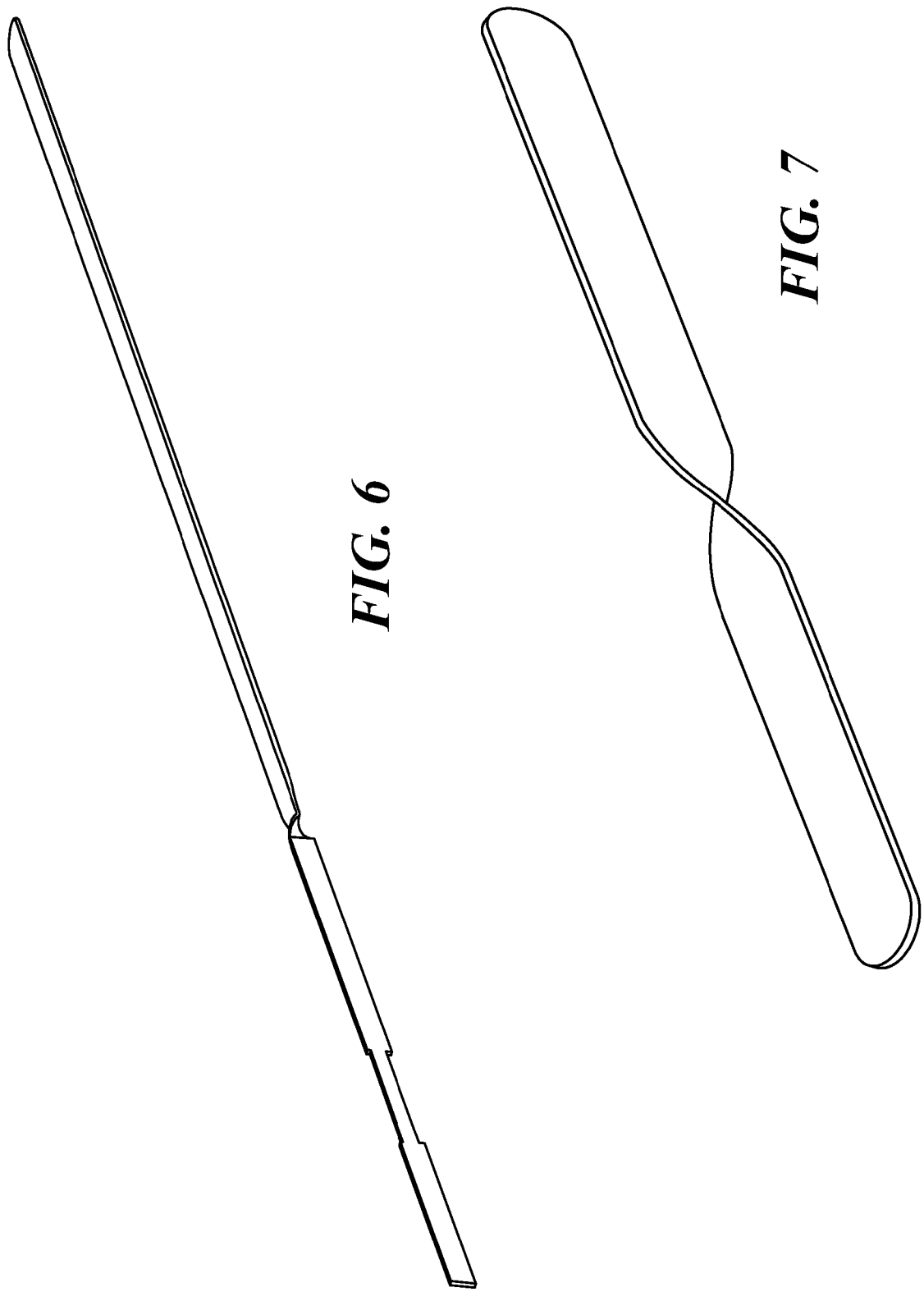

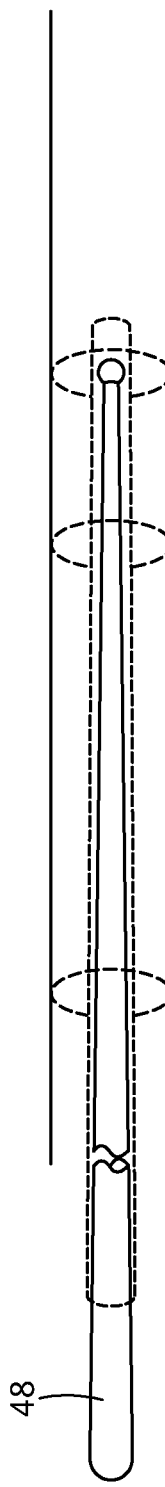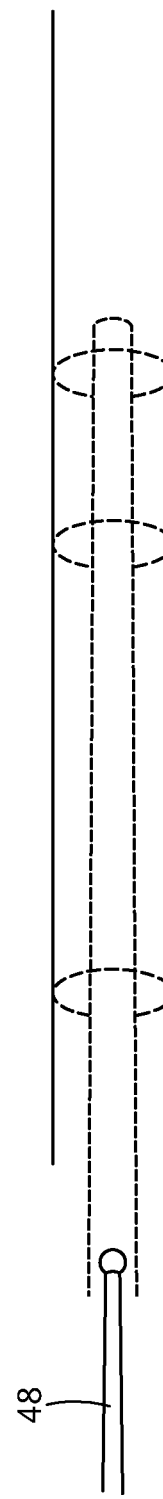
FIG. 9
FIG. 10

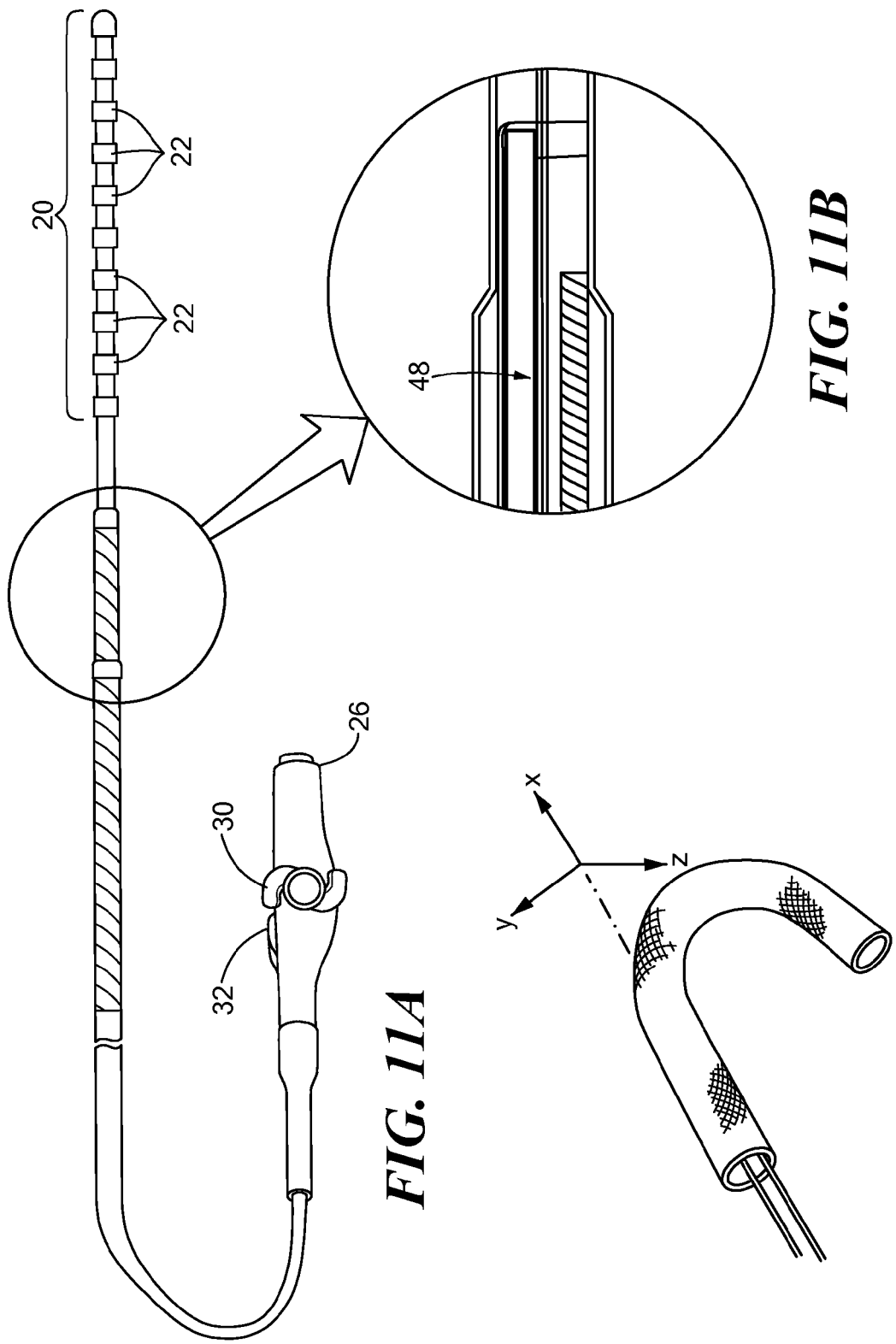

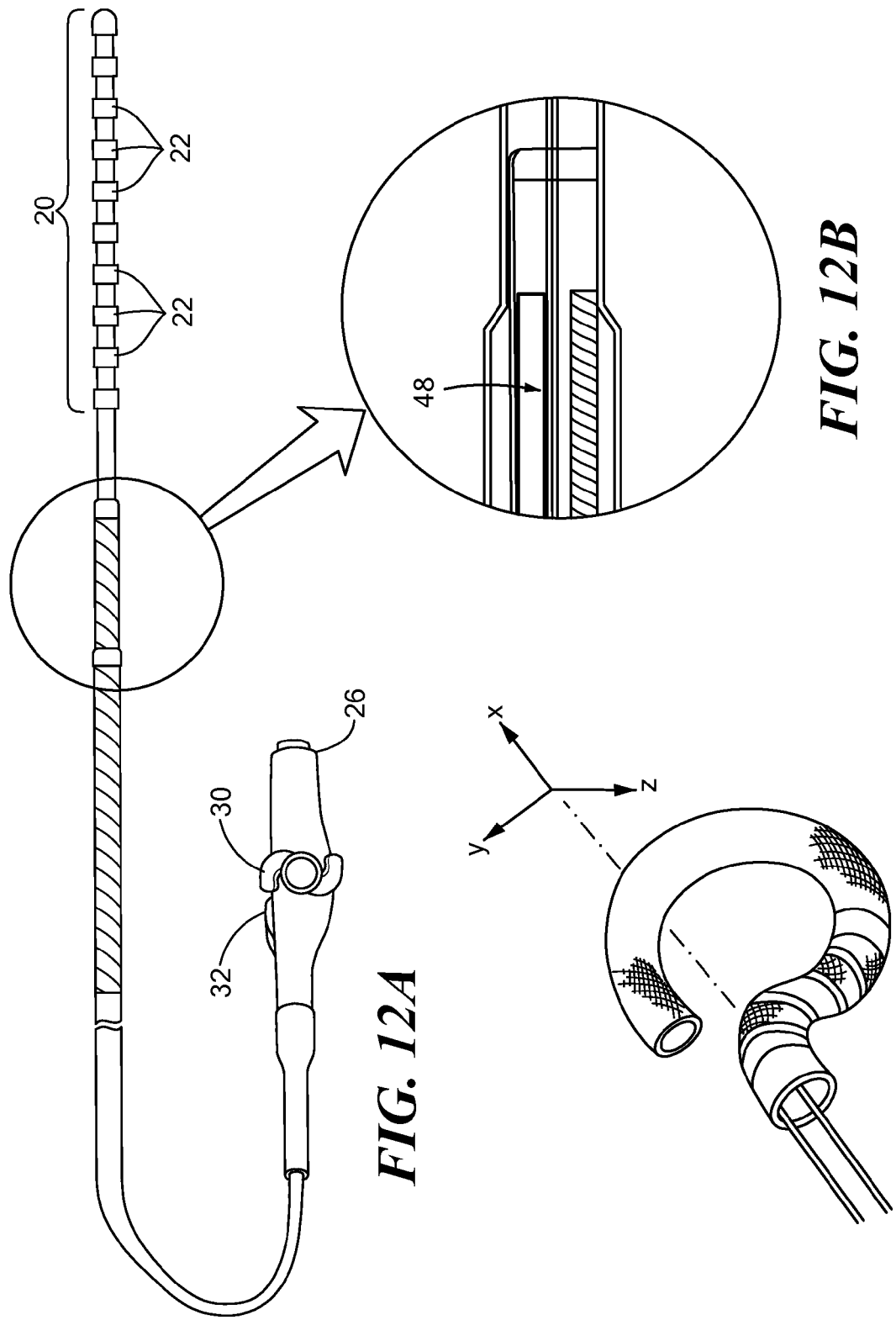

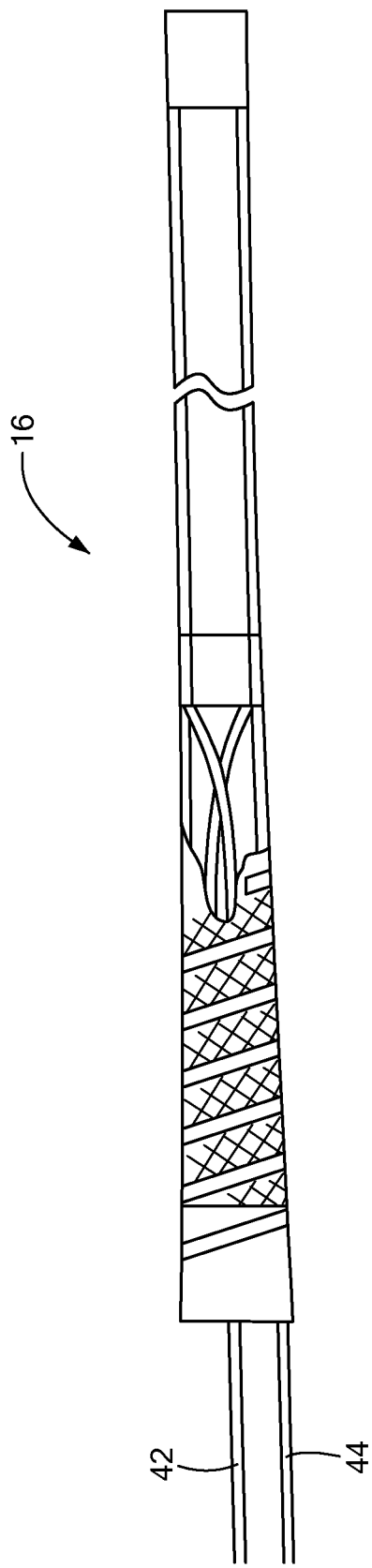
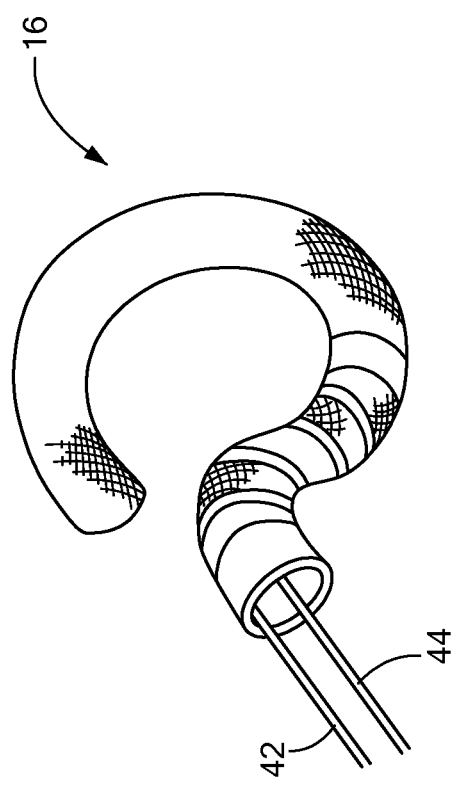
FIG. 13A
FIG. 13B

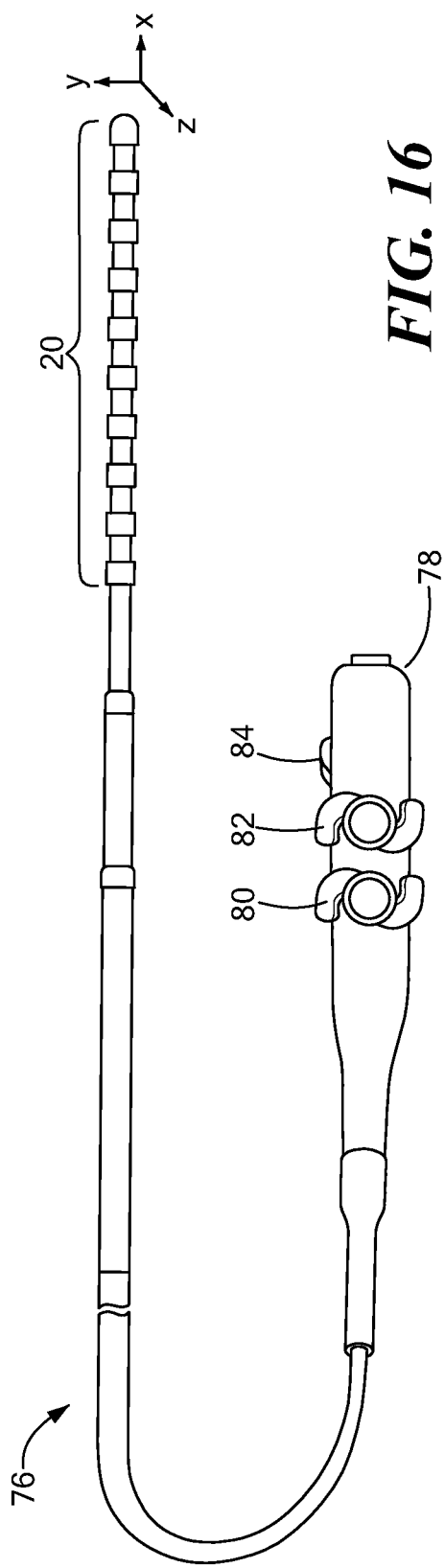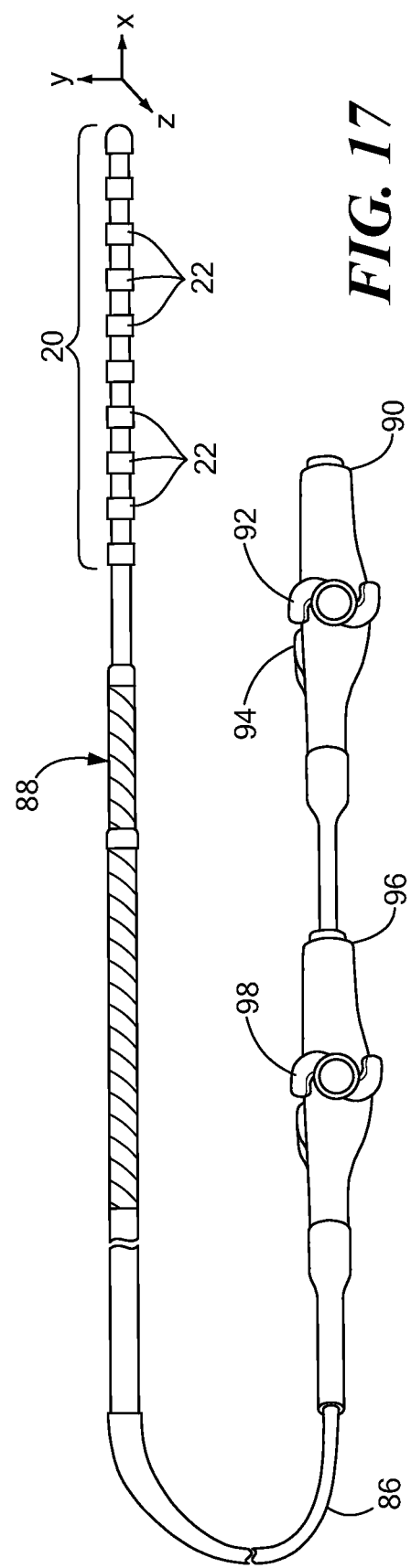

BI-MODAL LINEAR AND LOOP ABLATION CATHETER, AND METHOD

CROSS-REFERENCE TO RELATED APPLICATION

Not applicable.

STATEMENT REGARDING FEDERALLY SPONSORED RESEARCH OR DEVELOPMENT

Not applicable.

FIELD OF THE INVENTION

The present invention relates generally to medical devices, and more particularly to steerable catheters, systems, and methods for treating patients through ablation of tissue.

BACKGROUND OF THE INVENTION

Numerous procedures involving catheters and other minimally invasive devices may be performed to provide a wide variety of medical treatments, such as ablation, angioplasty, dilation and others. The term "atrial fibrillation" is a type of cardiac arrhythmia, or irregular heartbeat, in which the atria fail to contract effectively. Normal sinus rhythm of the heart begins with an electrical impulse generated by the sinus node that propagates across the right and left atria (the two small upper chambers of the heart) to the atrioventricular node. Atrial contraction leads to pumping blood into the ventricles in synchronization with the electrical pulse.

During atrial fibrillation, disorganized electrical conduction in the atria causes rapid uncoordinated contractions, resulting in sub-optimal pumping of blood into the ventricle. The atrioventricular node may receive sporadic electrical impulses from many locations throughout the atria, instead of only from the sinus node. This electrical confusion may overwhelm the atrioventricular node, producing an irregular and rapid heartbeat. Consequently, blood may pool in the atria and increase a risk for blood clots.

While there are numerous variations of atrial fibrillation with different causes, they all involve irregularities in the transmission of electrical impulses through the heart. As a result, the heart does not pump the blood properly, and it may pool and clot. If a blood clot forms and moves to an artery in the brain, atrial fibrillation can lead to stroke.

The major risk factors for atrial fibrillation include age, coronary artery disease, rheumatic heart disease, hypertension, diabetes, and thyrotoxicosis. Atrial fibrillation affects 7% of the population over 65 years of age, and is also associated with increased risks of congestive heart failure and cardiomyopathy, which warrant medical attention and treatment. Atrial fibrillation is the most common sustained heart rhythm disorder and increases the risk for heart disease and stroke, both leading causes of death in the United States.

To treat cardiac arrhythmias including atrial fibrillation, physicians often employ specialized ablation catheters to gain access into interior regions of the body. Such catheters often include tip electrodes or other ablating elements used to create ablation lesions that physiologically alter the ablated tissue without removal thereof, and thereby disrupt or block electrical pathways through the targeted tissue.

In the treatment of cardiac arrhythmias, a specific area of cardiac tissue having aberrant electrically conductive pathways, such as atrial rotors, emitting or conducting erratic electrical impulses, may be initially localized. A physician may direct a catheter through a main vein or artery into the interior region of the heart that is to be treated. The ablating portion of the selected device is next placed near the targeted cardiac tissue that is to be ablated, such as a pulmonary vein ostium or atrium.

An ablation procedure may involve creating a series of inter-connecting lesions, to electrically isolate tissue believed to be the source of an arrhythmia. During such a procedure, a physician may employ several different catheters having variations in geometry and dimensions of the ablative element in order to produce the desired ablation pattern. Multiple devices having varying dimensions and shapes may also be used, to account for variations in anatomy. Each catheter may have a unique geometry for creating a specific lesion pattern or size, with the multiple catheters being sequentially removed and replaced to create the desired multiple lesions.

For example, some catheters may be capable of following a two-dimensional curve, which may be referred to as "curvilinear" or "linear" ablation. Other catheters may be capable of forming a three-dimensional shape, such as a loop that is almost transverse to the catheter's longitudinal axis, which may be referred to as "loop" ablation.

Accordingly, it is desirable to provide a single medical device capable of both linear and loop ablation, thereby reducing the need for additional medical devices.

SUMMARY OF THE INVENTION

The present invention advantageously provides medical devices, systems, and methods for treating patients with tissue ablation. In particular, catheter systems are provided having bi-modal steering mechanisms, which are capable of both linear and loop ablation. The catheter system may have two different steering modes: two-dimensional and three-dimensional. In the first and second steering modes, the steering actuator may cause one or more portions of the catheter shaft to bend in different planes. A steerable ablation catheter may include treatment elements such as electrodes at its distal end and along the catheter shaft, each of which may map, pace, and ablate. Optional features include a series of thermocouples for monitoring local temperatures.

Methods for ablating a tissue region are also provided, including directing a treatment assembly of a medical device toward a tissue region, and the treatment element may include a series or an array of electrodes; selecting a first or second steering mode; in the first steering mode, manipulating a steering actuator from an initial position to cause a first portion of the catheter body to bend from an initial shape to a first arc shape along a first plane; in the second steering mode, manipulating the steering actuator from the initial position to cause the first portion to bend from the initial shape to a second arc shape, and to cause a second portion of the catheter body to bend along a second plane; and delivering ablative energy to the treatment assembly. The method may also include monitoring an electrical signal of the tissue region, such as a cardiac tissue region, or monitoring temperatures of the electrodes.

A more complete understanding of the present invention, and its associated advantages and features, will be more readily understood by reference to the following description and claims, when considered in conjunction with the accompanying drawings.

BRIEF DESCRIPTION OF THE DRAWINGS

In this description, reference will be made to the attached drawings:

FIGS. 6 and 7 are partial perspective views of additional guide plates;

FIGS. 9 and 10 are partial views, showing different positions of a stiffening wire;

FIGS. 11A-12C are partial cross-section views of the catheter of FIG. 8, showing different steering modes;

FIGS. 13A and 13B are partial cross-section views of the catheter shaft of FIG. 8;

FIGS. 14A-15 are partial views of catheters, showing loop steering;

FIGS. 16 and 17 are side elevation views of a third and fourth catheter embodiment;

DETAILED DESCRIPTION OF THE INVENTION

Figure 1:
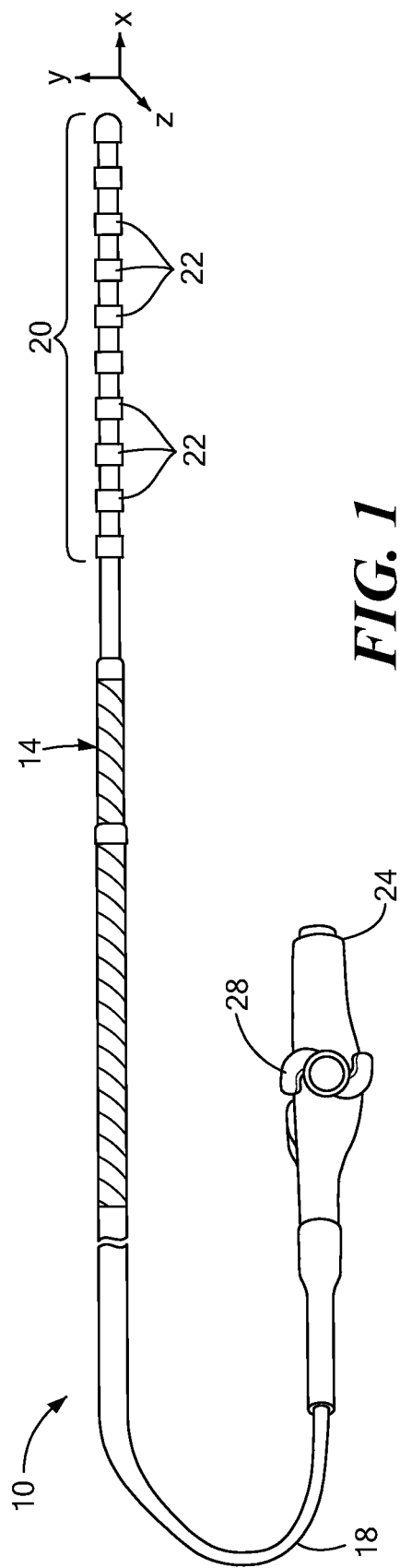
FIG. 1 is a side elevation view of a first catheter embodiment.

The present invention advantageously provides medical devices, systems, and methods for treating patients, in particular with catheter systems having bi-modal steering mechanisms, which are capable of both linear and loop ablation.

Referring to the drawings, the present invention provides various embodiments of medical devices for treating patients, which may be in the form of catheters having more than one steering mode. The illustrations of course depict only some of many different possible catheter designs that are within the scope of the present invention. For clarity and convenience, the present detailed description will only describe a few embodiments.

The catheters of the present invention may be sized and dimensioned for intraluminal and transseptal access to a patient's heart for the treatment or ablation thereof. Some of these embodiments are in the form of catheters generally designated at reference numerals 10 and 12, and catheter shaft designs generally designated at reference numerals 14 and 16.

A first example embodiment of the present invention is shown in FIG. 1. Medical device 10 may generally define an elongated, flexible catheter body 18 with proximal and distal ends having a distal treatment assembly 20 that may include a series of electrodes 22, as well as a handle assembly 24 at a proximal end or portion of the catheter body 18. The catheter body 18 may be formed and dimensioned to provide sufficient column and torsional strength to support standard interventional procedures such as those which access the vasculature from a femoral vein or artery and further access the patient's heart. The catheter shaft may include reinforcement elements or otherwise be constructed to provide desired degrees of stiffness, flexibility, and torque transmission along the length of the body and at selected locations along its length. For example, the catheter body may have portions or components of differing size, thickness or flexibility, and may include wires, braiding, changes in wall thickness, additional wall layers or catheter body components, sleeves, or other components reinforcing or otherwise supplementing an outer wall or thickness along its length. Some portions that may experience significant loading or torque during a particular procedure may also include reinforcement.

FIG. 1 depicts medical device 10 having a handle assembly 24 with a knob or steering actuator 28. Steering actuator 28 may have an initial or neutral position, and may be moved in one direction to a first position, and in another direction to a second position. The catheter shaft may have portions of relatively higher and lower flexibility, and may have a proximal portion of a larger size than a distal portion.

Figure 2:
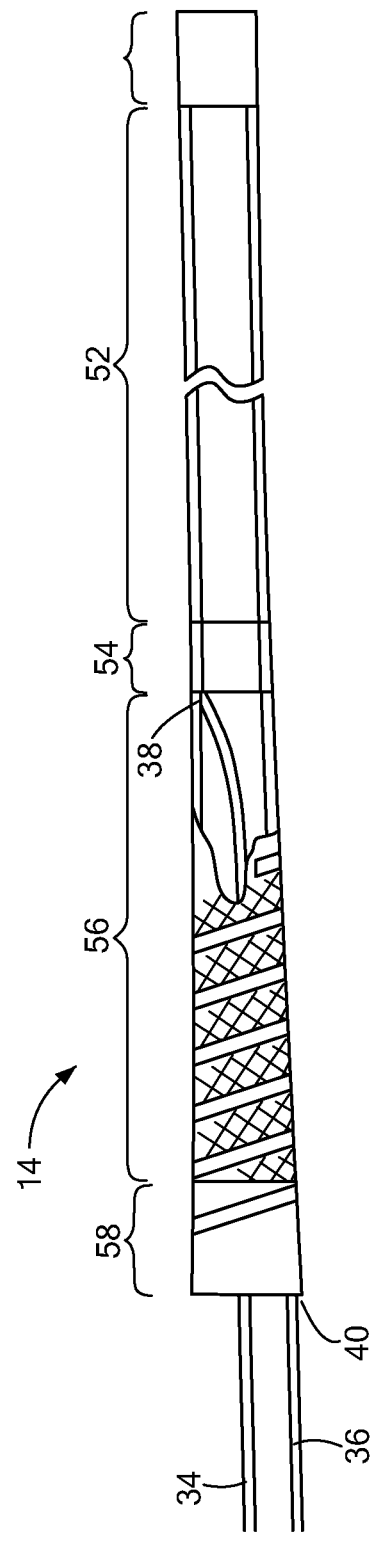
FIG. 2 is a partial cross-section view of the catheter shaft of FIG. 1, showing different steering modes.

The catheter shaft design of this first example embodiment is shown in FIG. 2. A first and second steering member or wire 34 and 36 are depicted, affixed to radially or diametrically opposite sides of the catheter body 18. First and second steering wires 34 and 36 have proximal ends coupled to steering actuator 28 for selectively pulling either steering wire. The steering wires 34 and 36 are generally free from attachment to other catheter components up to a first and second attachment point 38 and 40, which are at different longitudinal positions. These different attachment points enable the same steering actuator 28 to select and operate the catheter in a first steering mode by twisting or moving steering actuator 28 in a first direction, and to select and operate the catheter in a second steering mode by twisting or moving steering actuator 28 in a second direction. Accordingly, a single steering actuator 28 can provide two different steering modes, either two-dimensional or three-dimensional.

The catheter body may also have at least four portions of alternating higher and lower flexibility 52, 54, 56 and 58. The distal portion of higher flexibility 52 may encompass the treatment assembly 20, for example including all of the electrodes 22, and this portion may be what bends to form the curved shape of the two-dimensional steering mode, and to form the loop of the three-dimensional steering mode. The proximal portion of higher flexibility 56 may encompass bending in the three-dimensional steering mode, to create the desired angle of the loop with respect to the longitudinal axis. In a specific example, the portions of higher flexibility may be polymers having durometers of 30-45 D, and the portions of lower flexibility may be polymers having durometers of 50-72 D.

Figure 3:
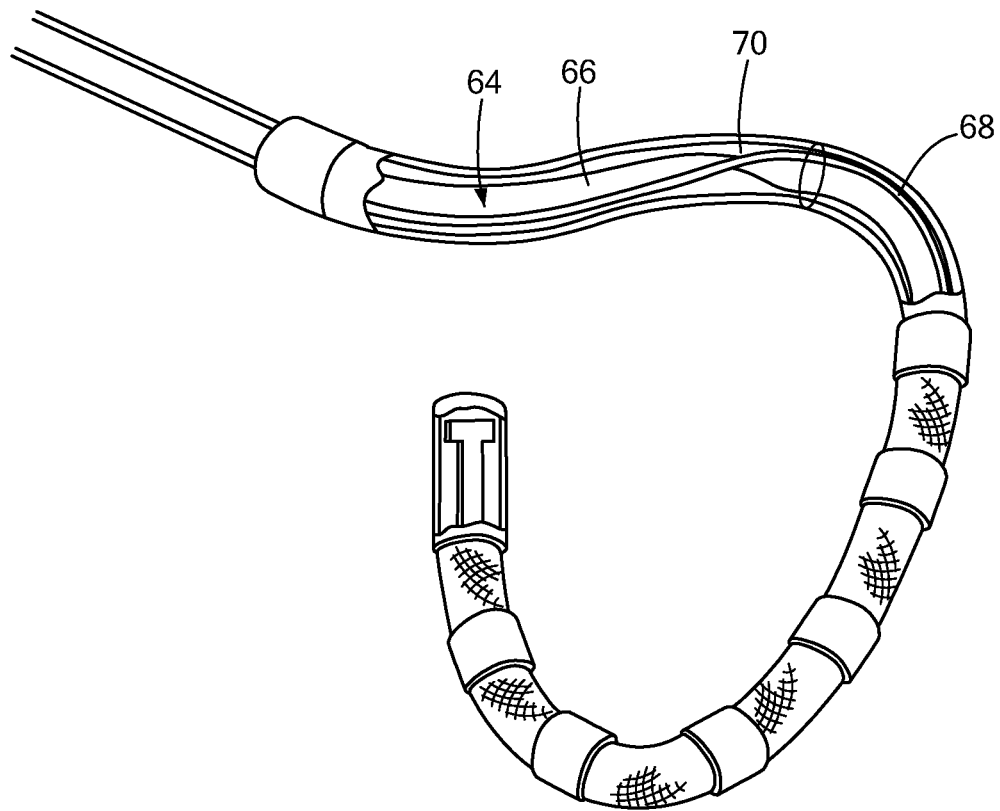
FIG. 3 is a partial cut-away view of a catheter, showing loop steering.
Figure 4:
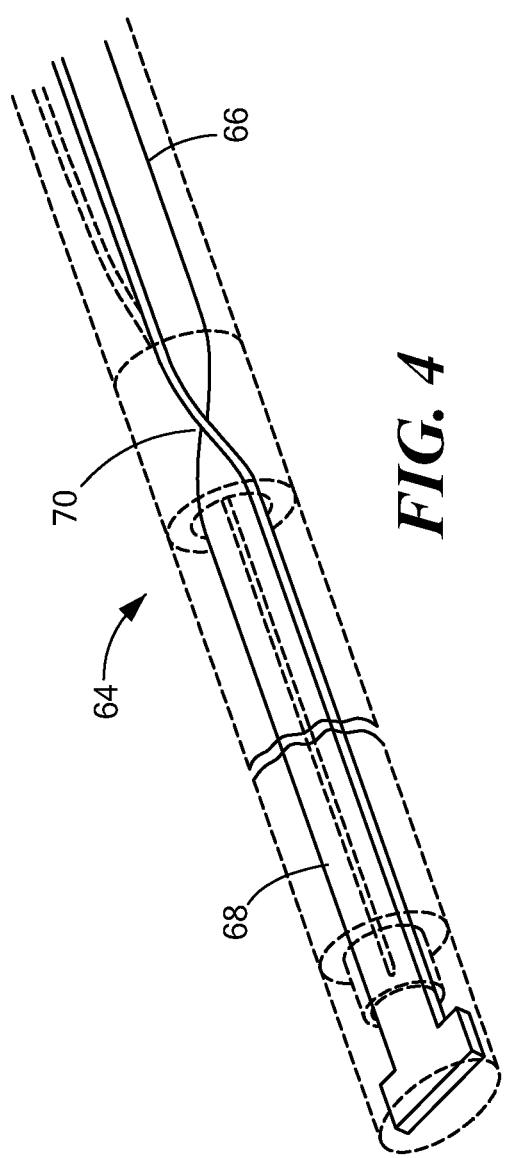
FIGS. 4 and 5 are partial perspective views of a guide plate.
Figure 5:
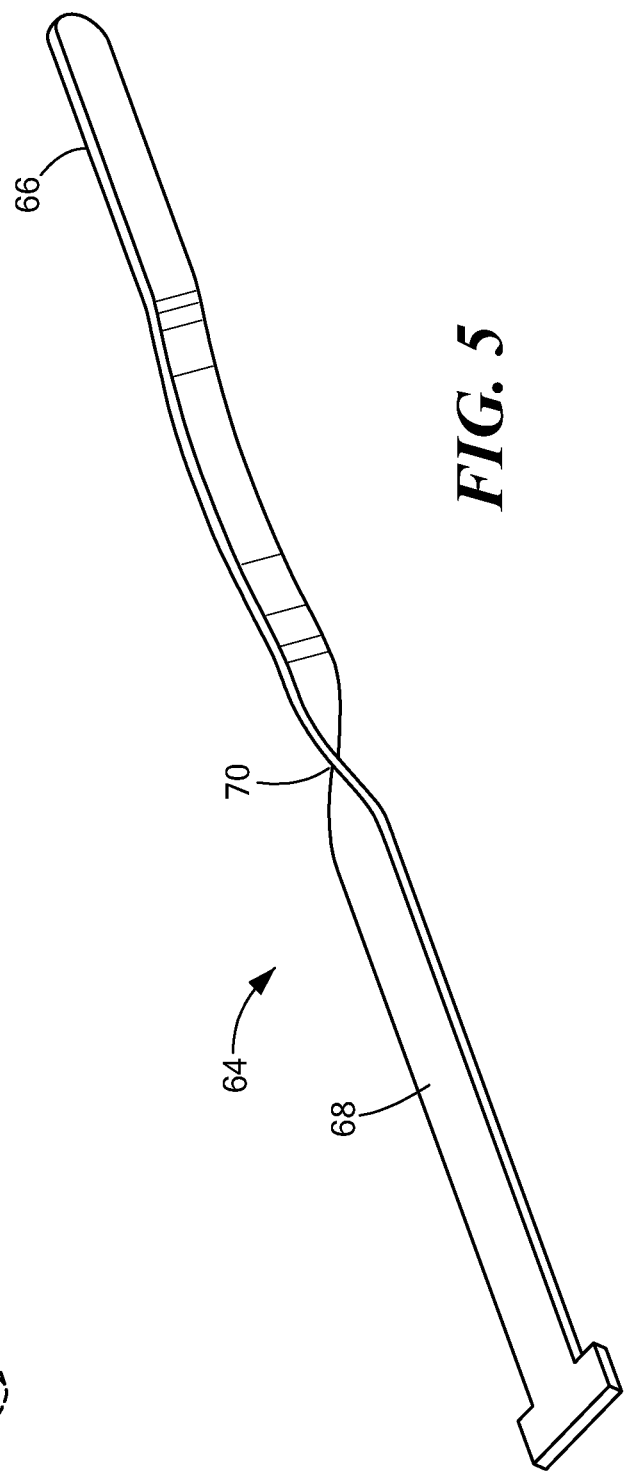

The catheters of the present invention may have a proximal and distal plane of preferential bending. This compound preferential bending may be achieved with a guide plate 64 as shown in FIGS. 3-5, having proximal and distal portions 66 and 68 and a transition portion 70. Transition portion 70 may have the illustrated twisted shape, and the angle may be selected as desired, which may for example be 90 degrees. The proximal portion 66 of guide plate may optionally have a curved or concave section, which may be provided to bias the catheter shaft during the three-dimensional steering mode. Additional possible designs for guide plates are shown in FIGS. 6 and 7.

Figure 2A:
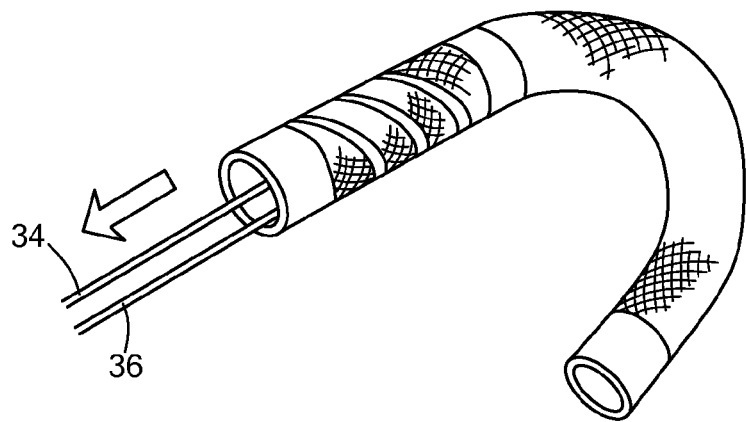
FIGS. 2A-2C are partial perspective views of a catheter, showing loop steering.

In operation, the steering actuator 28 may initially be in a neutral position, and the distal catheter shaft will be generally straight (with the possible exception of a curved or concave section of a guide plate), though it will of course tend to follow the shape of any body passage or lumen. FIG. 1 illustrates the treatment assembly 20 as generally following an x-axis. For linear ablation, or at any time two-dimensional steering is desired according to the first steering mode, the steering actuator 28 may be moved or rotated in a first direction to a first position, thus pulling on first steering member 34 and causing distal portion 68 of guide plate 64 inside the catheter body's distal portion of higher flexibility 52 to bend in the distal plane of preferential bending. This bending may be toward the y-axis of FIG. 1, into a shape illustrated in FIG. 2A. In the two-dimensional steering mode, the term "linear" of course includes curving lines, as shown in FIG. 2A.

Figure 2B:
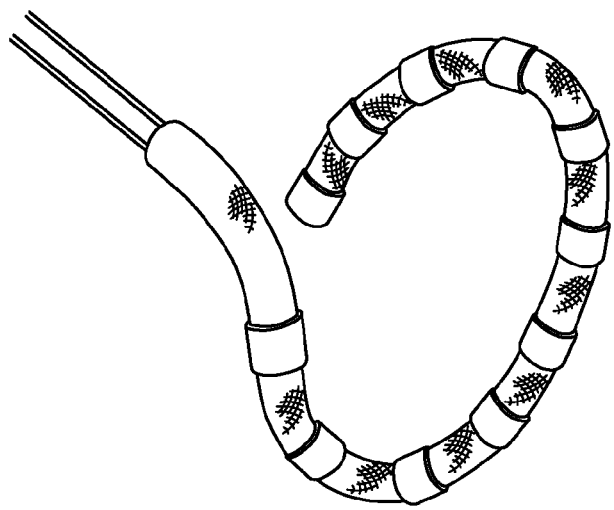
Figure 2C:
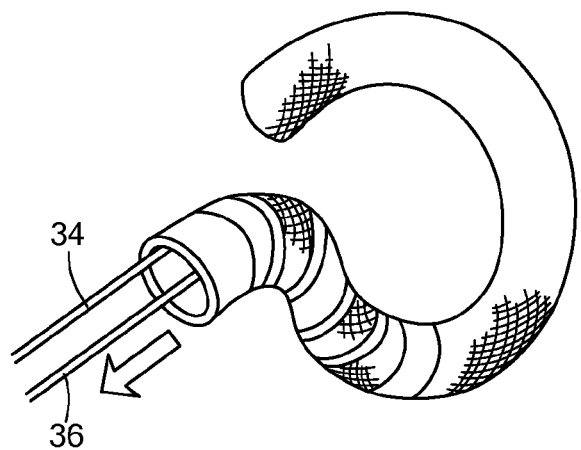

For loop ablation, or at any time three-dimensional steering is desired according to the second steering mode, the steering actuator 28 may be moved or rotated in a second direction to a second position, thus pulling on second steering member 36. In this second steering mode, distal portion 68 of guide plate 64 inside the catheter body's distal portion of higher flexibility 52 will bend in the distal plane of preferential bending, but in the opposite direction as illustrated in FIGS. 2B and 2C. Simultaneously, proximal portion 66 of guide plate 64 inside the catheter body's proximal portion of higher flexibility 56 will bend in the proximal plane of preferential bending.

In this three-dimensional steering mode, a distal portion of catheter body may be formed into a loop as shown in FIGS. 2B and 2C, and a more proximal portion of catheter body may bend toward the z-axis of FIG. 1, such that the loop defines an angle with respect to the longitudinal axis of an adjacent portion of catheter body. This angle may have whatever magnitude the physician prefers, including 90 degrees. An angle somewhat less than perpendicular may be selected, to provide a measure of resilience or tactile feedback when contacting tissue.

Figure 8:
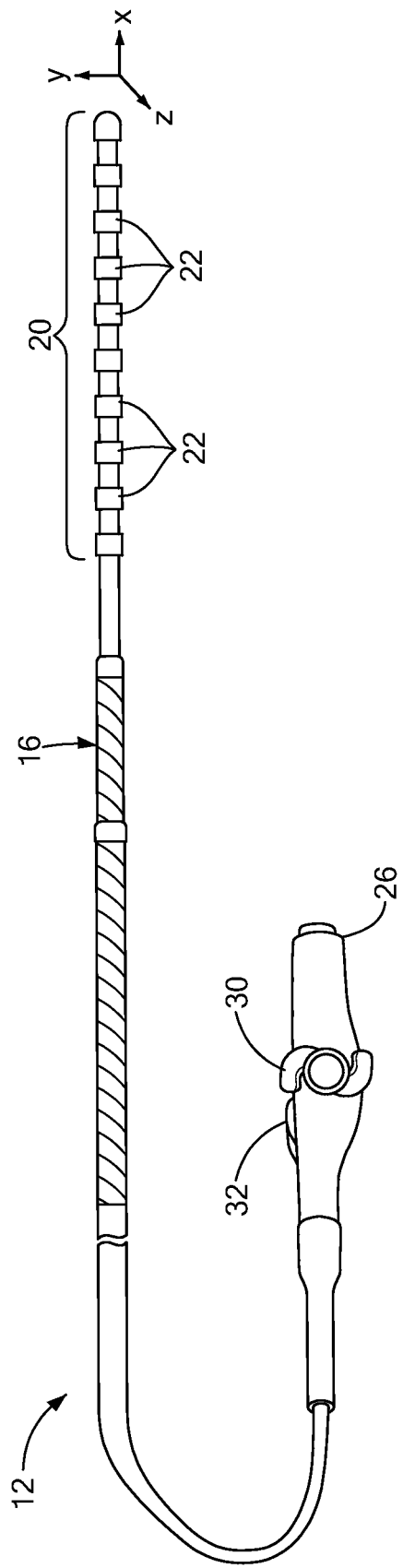
FIG. 8 is a side elevation view of a second catheter embodiment.
Figures 14A, 14B:
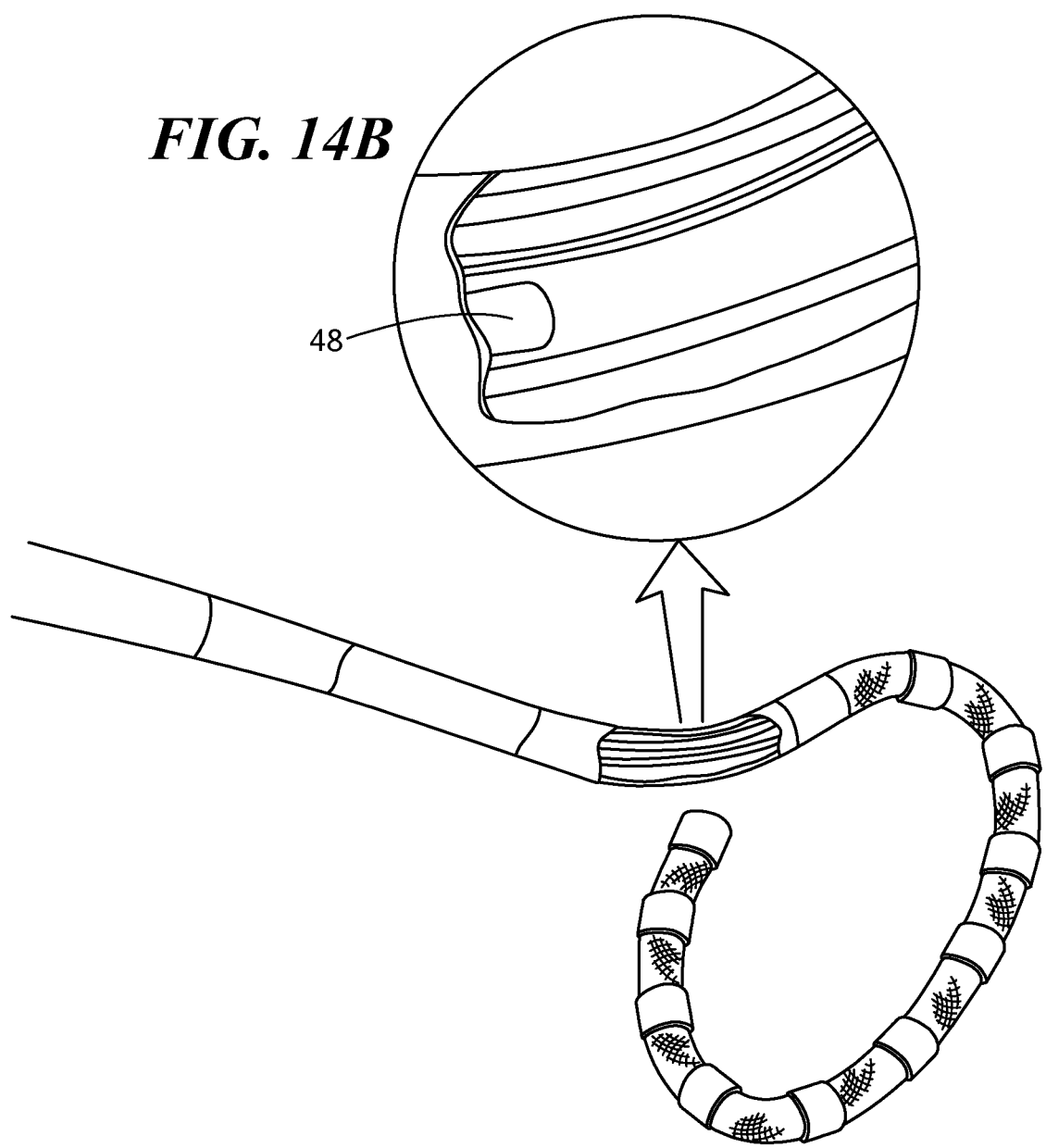

Another example embodiment of a medical device according to the present invention is shown in FIG. 8, having a bi-directional shaft design with a discrete mechanism for selecting between different steering modes. Catheter 12 is generally similar to catheter 10 with a handle assembly 26 having a steering knob or actuator 30 as well as an additional controller, such as for example slider 32, and a different catheter shaft design 16.

This mechanism for selecting different steering modes may be in the form of a movable stiffener 48, shown in FIGS. 9-12C. The stiffener 48 may be moved to the distal position of FIGS. 9 and 11A-11C, selecting a first mode of steering, or to the proximal position of FIGS. 10 and 12A-12C, thus selecting a second steering mode. In the first steering mode of FIGS. 9 and 11A-11C, stiffener 48 may oppose bending of the proximal portion 66 of the guide plate 64, which may be referred to as two-dimensional or "linear" steering. On the other hand, in the second steering mode of FIGS. 10 and 12A-12C, stiffener 48 is retracted proximally and allows bending of the proximal portion 66 of the guide plate 64 (toward the z-axis for example), which may be referred to as three-dimensional or "loop" steering.

The catheter shaft design of this second example embodiment is shown in FIGS. 13A and 13B, depicting another pair of first and second steering wires 42 and 44, affixed to radially or diametrically opposite sides of the catheter body at the same longitudinal position 46. First and second steering wires 42 and 44 have proximal ends coupled to steering knob 30 for selectively pulling either steering wire. The steering wires 42 and 44 are generally free from attachment to other catheter components up to attachment points 46. With both of the steering wires 42 and 44 acting on the same longitudinal position, the steering actuator 30 is operable to bend the catheter shaft in a first and second direction by twisting or moving the steering actuator in a first and second direction, respectively, in both a first and second steering mode.

In embodiments having the bi-directional shaft design, the stiffener 48 is coupled at its proximal end with a controller, such as for example slider 32 shown in FIG. 8, which is operable to move stiffener between the distal position of FIGS. 9 and 11A-11C and the proximal position of FIGS. 10 and 12A-12C. This bi-directional shaft design also allows hybrid steering modes: by moving the stiffener 48 to intermediate positions between the proximal and distal positions, combinations of the first and second steering modes may be achieved.

Figure 15:
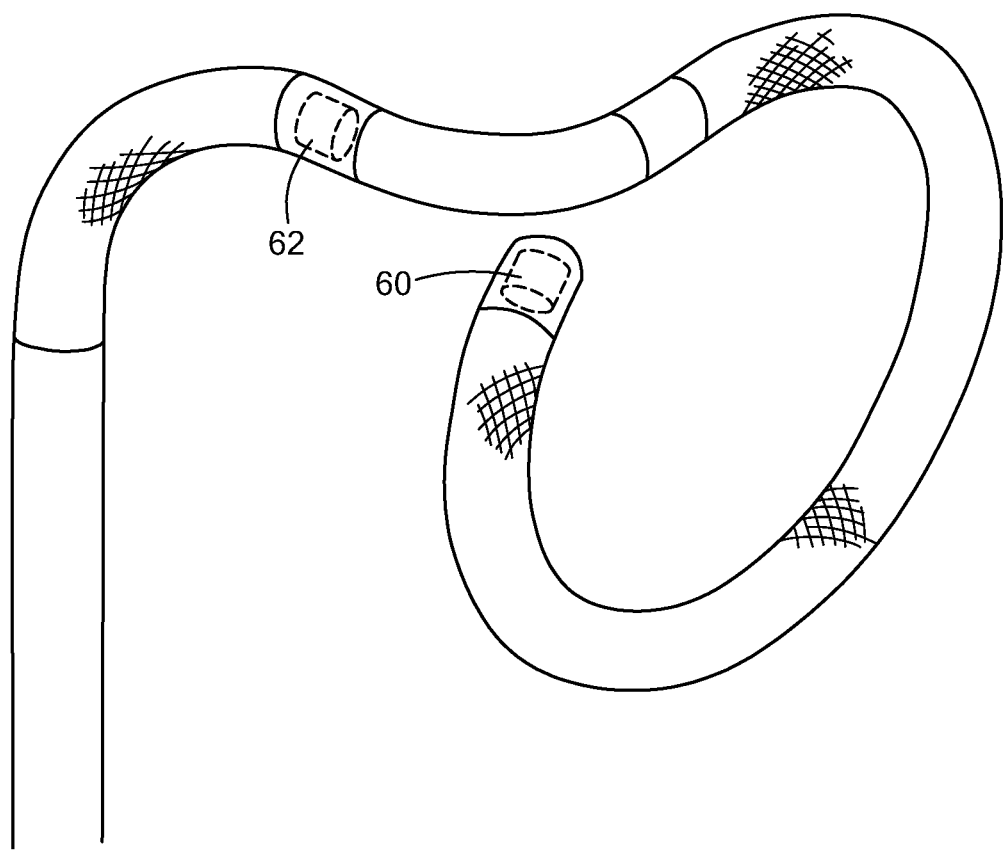

Additional optional components for catheter shafts according to the present invention may include reinforcements such as for example a braid or coil embedded in or affixed to the catheter body, which may be made of any suitable material including metals and strong polymers. Specific examples of reinforcing materials may include stainless steel and nitinol. These reinforcing components may also be used to more strongly affix the steering wires to the catheter body, such as for example by embedding them into the wall of catheter body, inside or outside of (or even woven among) reinforcing components. FIG. 15 also illustrates optional anchoring components, which may include a first and second anchoring ring 60 and 62, and which may be used to affix the steering wires to the catheter body.

Another example embodiment of a medical device according to the present invention is shown in FIG. 16, having a supplemental steering mechanism for more agile manipulation of the distal assembly. Catheter 76 has a handle assembly 78 having a first and second steering knob or actuator 80 and 82. First steering actuator 80 may be generally similar to steering actuator 28 of catheter 10, or may be generally similar to steering actuator 30 of catheter 12 with the addition of optional slider 84 for controlling a stiffener.

Second steering actuator 82 may be used to bend and steer a more proximal portion of the catheter shaft, to more deftly position the distal assembly near a desired site of tissue for treatment. In catheter shaft designs having at least four alternating portions of higher and lower flexibility, the second steering actuator 82 may enable bending and steering of a supplemental steering portion, which is proximal of the proximal portion of higher flexibility.

Another example embodiment of a medical device according to the present invention is shown in FIG. 17, having a supplemental steering mechanism in the form of a steerable catheter sheath 86, which at least partially surrounds an ablation catheter 88 according to the present invention. Catheter 88 has a handle assembly 90 having a steering knob or actuator 92, and may have an optional slider 94. Catheter sheath 86 has a handle assembly 96 with a sheath steering knob or actuator 98. Catheter 88 and catheter sheath 86 may be moved, more specifically advanced, retracted or rotated, with respect to each other. The sheath steering actuator 98 may be used to bend and steer a selected portion of the catheter shaft, and sheath 86 may be moved so as to steer different portions of the catheter shaft.

Figure 18:
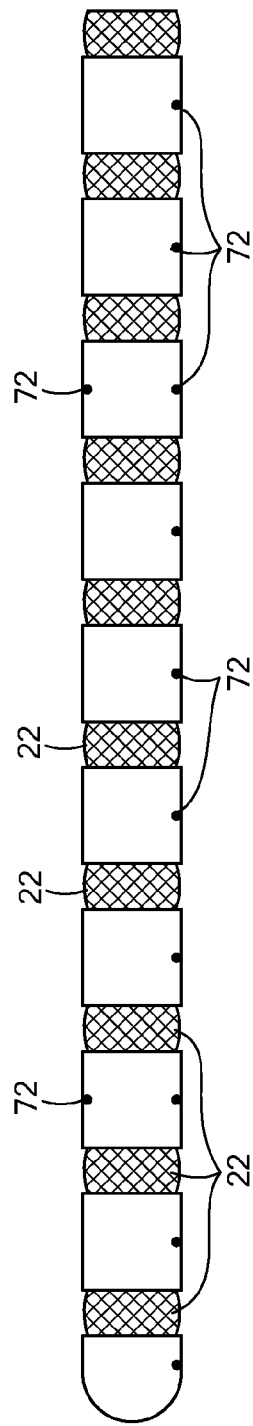
FIGS. 18 and 19 are partially diagrammatic views of catheters having thermocouples.
Figure 19:
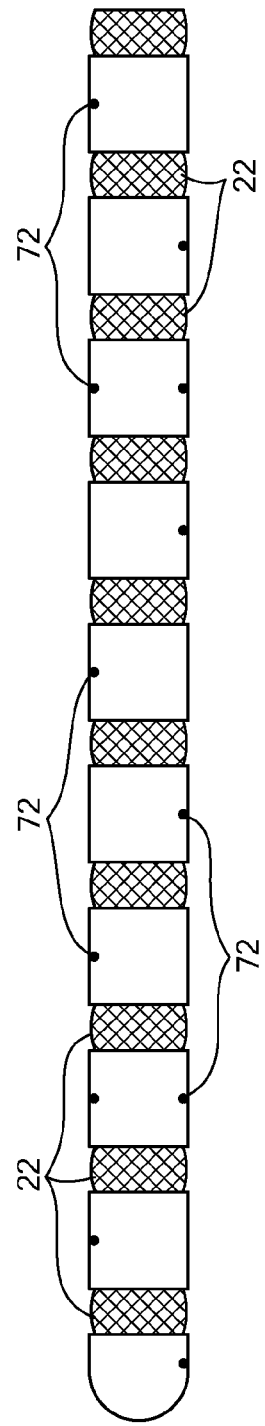

Now referring to FIGS. 18 and 19, the distal treatment assembly 20 provides for the treatment, monitoring, or otherwise clinically interacting with a desired tissue region, such as the heart. The treatment assembly 20 may include, for example, an array or series of electrodes 22 disposed near, on, or substantially on the distal end of the catheter body. The electrodes 22 may be mounted to detect electrical signals between any pair of electrodes (bi-pole) for mapping of electrical activity, and/or for performing other functions such as pacing of the heart. Moreover, the electrodes 22 may deliver ablation energy across an electrode pair or from independent electrodes when delivering monopolar energy. In a particular example, the plurality of electrodes may include from eight to twelve electrodes, with either symmetric or asymmetric spacing. The electrodes 22 may be constructed from platinum, iridium, or any other suitable material.

Figure 20:
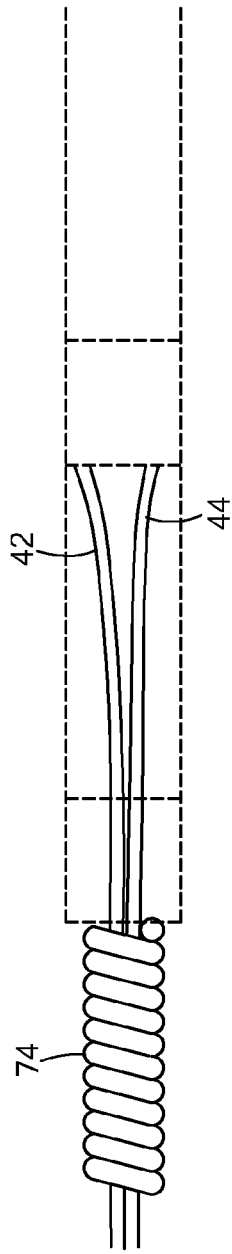
FIG. 20 is a partial view some catheter components.

Each electrode 22 may include a temperature sensor or thermocouple 72 located on or near the tissue side of the electrode, to monitor the temperature at each ablation site before and during ablation. Indeed, each electrode 22 may have a pair of thermocouples at radially or diametrically opposite points. The thermocouples are electrically connected to the handle assembly by conduits or wires, which may optionally be at least partially surrounded by a coil 74 shown in FIG. 20 to improve signal fidelity. To reduce the quantity of thermocouples and associated wires, fewer thermocouples may be used and arranged specifically to still provide good performance. For example, a quantity of the temperature sensors is at least equal to a quantity of the electrodes, and is at most twice the quantity of electrodes. A more detailed example includes at least eight electrodes, and at most twelve temperature sensors. In the specific examples depicted in FIGS. 18 and 19, ten electrodes and twelve thermocouples are depicted. The thermocouples shown in FIG. 18 are arranged generally on one radial side of the catheter body, with two thermocouples on the radially opposite side of the catheter body. In FIG. 19, the thermocouples are positioned on alternating radially opposite sides of the catheter body.

It should be understood that an unlimited number of configurations for the present invention could be realized. The foregoing discussion describes merely exemplary embodiments illustrating the principles of the present invention, the scope of which is recited in the following claims. In addition, unless otherwise stated, all of the accompanying drawings are not to scale. Those skilled in the art will readily recognize from the description, claims, and drawings that numerous changes and modifications can be made without departing from the spirit and scope of the invention.

What is claimed is:

1. A medical device, comprising:
   a catheter body having a first portion with a first plane of preferential bending, and a second portion with a second plane of preferential bending, the first portion being distal of the second portion;
   a single steering actuator coupled to the catheter body;
   a guide plate within the catheter body, the guide plate having a first outer edge, a second outer edge, a longitudinal axis, a width that extends directly from the first outer edge directly to the second outer edge and that is perpendicular to the longitudinal axis, a length that is located along the longitudinal axis, a proximal portion, a distal portion, and a transition portion, the guide plate proximal portion being configured to cause the second plane of preferential bending and the distal portion of the guide plate being configured to cause the first plane of preferential bending, the proximal portion having a distal section, a proximal section, and a middle section located directly between the distal section and the proximal section, the middle section having a width that extends directly from the first outer edge of the guide plate directly to the second outer edge of the guide plate, the distal section and the proximal section being linear and located along the guide plate longitudinal axis and an entirety of the middle section having an arc of curvature when the catheter body is in an at least substantially linear configuration; and
   a first steering member and a second steering member, each of the first and second steering members having a proximal end and a distal end, the proximal end of each of the first and second steering members being coupled with the single steering actuator, and the distal end of each of the first and second steering members being directly affixed to the catheter body,
   the medical device having a first and second mode of steering:
   in the first mode of steering, movement of the single steering actuator from an initial position is configured to cause the first portion to bend from an initial shape to a first arc shape along the first plane of preferential bending; and
   in the second mode of steering, movement of the single steering actuator from the initial position is configured to cause the first portion to bend from the initial shape to a second arc shape along the second plane of preferential bending.

2. The medical device of claim 1, further comprising a plurality of electrodes affixed to the first portion of the catheter body.

3. The medical device of claim 2, wherein each of the plurality of electrodes is capable of mapping, pacing and ablating.

4. The medical device of claim 2, further comprising a plurality of temperature sensors, wherein a quantity of the plurality of temperature sensors is at least equal to a quantity of the plurality of electrodes, and is at most twice the quantity of the plurality of electrodes.

5. The medical device of claim 4, wherein the quantity of the plurality of electrodes is at least eight, and the quantity of the plurality of temperature sensors is at most twelve.

6. The medical device of claim 1, wherein the first and second planes of preferential bending are approximately perpendicular.

7. The medical device of claim 1, wherein the proximal portion of the guide plate and the distal portion of the guide plate are substantially coextensive with the first and second portions of the catheter body, respectively; wherein the guide plate proximal portion and the guide plate distal portion are generally planar, and are connected by the transition portion.

8. The medical device of claim 7, wherein the catheter body has at least four portions of alternating higher and lower flexibility; the transition portion of the guide plate being positioned within a distal portion of higher flexibility of the at least four portions of alternating higher and lower flexibility.

9. The medical device of claim 1, wherein the first mode of steering is configured to be selected by moving the single steering actuator from the initial position in a first direction, and the second mode of steering is configured to be selected by moving the single steering actuator from the initial position in a second direction.

10. The medical device of claim 1, wherein the distal ends of the first and second steering members are affixed to radially opposite sides of the catheter body at one longitudinal position.

11. The medical device of claim 1, wherein the distal ends of the first and second steering members are directly affixed to radially opposite sides of the catheter body at different longitudinal positions.

12. The medical device of claim 1, wherein the first and second steering members both extend to a catheter body distal end.

* * * * *